United States Patent
Capuzzi et al.

(10) Patent No.: US 11,292,978 B2
(45) Date of Patent: Apr. 5, 2022

(54) LOW POUR POINT TRIMETHYLOLPROPANE ESTERS

(71) Applicant: Novamont S.p.A., Novara (IT)

(72) Inventors: Luigi Capuzzi, Novara (IT); Francesca Digioia, Barengo (IT); Angela Sagliano, Novara (IT)

(73) Assignee: NOVAMONT S.P.A., Novara (IT)

( * ) Notice: Subject to any disclaimer, the term of this patent is extended or adjusted under 35 U.S.C. 154(b) by 0 days.

(21) Appl. No.: 15/580,315

(22) PCT Filed: Jun. 10, 2016

(86) PCT No.: PCT/EP2016/063396
§ 371 (c)(1),
(2) Date: Dec. 7, 2017

(87) PCT Pub. No.: WO2016/198668
PCT Pub. Date: Dec. 15, 2016

(65) Prior Publication Data
US 2018/0163151 A1  Jun. 14, 2018

(30) Foreign Application Priority Data
Jun. 12, 2015 (IT) .......... 102015000023433

(51) Int. Cl.
| | |
|---|---|
| *C10M 105/38* | (2006.01) |
| *C10M 129/74* | (2006.01) |
| *C07C 67/03* | (2006.01) |
| *C07C 67/48* | (2006.01) |
| *C10M 105/34* | (2006.01) |
| *C10M 169/04* | (2006.01) |
| *C10M 171/02* | (2006.01) |
| *C10M 177/00* | (2006.01) |
| *C10N 20/02* | (2006.01) |
| *C10N 30/02* | (2006.01) |
| *C10N 40/16* | (2006.01) |

(52) U.S. Cl.
CPC .......... *C10M 105/38* (2013.01); *C07C 67/03* (2013.01); *C07C 67/48* (2013.01); *C10M 105/34* (2013.01); *C10M 129/74* (2013.01); *C10M 169/04* (2013.01); *C10M 171/02* (2013.01); *C10M 177/00* (2013.01); *C10M 2207/283* (2013.01); *C10M 2207/2835* (2013.01); *C10N 2020/02* (2013.01); *C10N 2030/02* (2013.01); *C10N 2040/16* (2013.01)

(58) Field of Classification Search
CPC .............. C10M 129/74; C10M 105/38; C10N 2240/201; C10N 2040/16; H01B 3/20
USPC .......................................... 508/485
See application file for complete search history.

(56) References Cited

U.S. PATENT DOCUMENTS

| | | | |
|---|---|---|---|
| 4,025,447 A | 5/1977 | Mancini et al. | |
| 4,175,046 A * | 11/1979 | Coant | C10M 111/04 508/485 |
| 4,826,633 A | 5/1989 | Carr et al. | |
| 5,202,044 A * | 4/1993 | Hagihara | C09K 5/045 252/67 |
| 5,470,497 A * | 11/1995 | Schlosberg | C09K 5/045 252/67 |
| 2004/0176261 A1* | 9/2004 | Tojou | C10M 105/38 508/485 |
| 2008/0033201 A1* | 2/2008 | Hof | C10M 105/38 560/201 |
| 2012/0190883 A1* | 7/2012 | Frey | C07C 67/08 560/182 |
| 2015/0090944 A1* | 4/2015 | Metzger | C10M 105/38 252/579 |
| 2015/0344400 A1* | 12/2015 | Frey | C07C 67/08 560/200 |
| 2016/0042830 A1* | 2/2016 | Ohno | H01B 3/22 252/570 |
| 2016/0055934 A1* | 2/2016 | Tagawa | C10M 101/025 585/16 |
| 2016/0355717 A1* | 12/2016 | Fukushima | F25B 31/002 |
| 2016/0355719 A1* | 12/2016 | Fukushima | C09K 5/045 |
| 2017/0009119 A1* | 1/2017 | Hahn | H01F 27/105 |
| 2018/0016518 A1* | 1/2018 | Kaneko | C10M 169/04 |
| 2018/0100119 A1* | 4/2018 | Aoyama | C10M 145/14 |

FOREIGN PATENT DOCUMENTS

| | | | | |
|---|---|---|---|---|
| GB | 1602092 | * 11/1981 | .............. | C10M 3/20 |
| JP | 2004-273291 A | 9/2004 | | |
| WO | WO-2005/118756 A1 | 12/2005 | | |
| WO | WO-2005118756 A1 | * 12/2005 | .......... | C10M 105/38 |

* cited by examiner

*Primary Examiner* — Ellen M McAvoy
(74) *Attorney, Agent, or Firm* — Polsinelli PC

(57) ABSTRACT

The present invention relates to polyol esters that are particularly suitable for use as insulating oils in electrical equipment where an effective cooling action is required, such as electrical transformers. In particular the invention relates to esters of trimethylolpropane with monocarboxylic acids of nine and/or ten carbon atoms, wherein the monocarboxylic acids of nine and/or ten carbon atoms comprise 5-15 mol % of branched acids and 85-95 mol % of linear acids with respect to the total moles of the monocarboxylic acids.

25 Claims, No Drawings

LOW POUR POINT TRIMETHYLOLPROPANE ESTERS

CROSS REFERENCE TO RELATED APPLICATIONS

This application is a National Phase filing under 35 U.S.C. § 371 of PCT/EP2016/063396 filed on Jun. 10, 2016; and this application claims priority to application No. 102015000023433 filed in Italy on Jun. 12, 2015 under 35 U.S.C. § 119. The entire contents of each application are hereby incorporated by reference.

This invention relates to polyol esters that are particularly suitable for use as insulating oils in electrical equipment where an effective cooling action is required, such as electrical transformers. These esters are in particular trimethylolpropane esters with monocarboxylic acids having nine and/or ten carbon atoms and a characteristic ratio between linear and branched chains which provide them with excellent properties in terms of viscosity, pour point and flash point.

The invention also relates to insulating oils containing the said esters, and electrical equipment comprising the said insulating oils.

The invention also relates to a method for the preparation of trimethylolpropane esters with a mixture of monocarboxylic acids having nine and/or ten carbon atoms and a characteristic molar ratio between linear and branched chains, and a method for preparing insulating oils having a kinematic viscosity at 40° C. which is below 35 mm$^2$/s, a pour point of below −40° C. and a flash point of over 200° C., even without the addition of additives influencing their high- and low-temperature behaviour.

Insulating oils are oils used, typically together with solid insulating materials, in electrical equipment for the purposes of electrical insulation, dissipating heat produced by the heating of circuits and protecting materials from the action of oxygen. The said insulating oils therefore have high thermal and chemical stability, resistance to oxidation, dielectric strength and thermal conductivity. They are therefore generally high performance fluids which may be intended for uses of various types according to their characteristics—for example oils with particularly high stability to oxidation are more suitable for use in high-power high-voltage transformers.

It is common practice to modulate the characteristics of insulating oils by means of suitable treatments or additives; for example stability to oxidation and electrical properties may be increased by restricting the presence of moisture and impurities and adding oxidation inhibitors.

Historically mineral oils (e.g. naphthenes) have been used as insulating oils, but recently these have increasingly been replaced by silicones, fluorinated or high molecular weight hydrocarbons and natural or synthetic ester-based oils. Ester-based oils in particular have fewer risks than mineral oils, for example lower flammability, greater tolerance to moisture and a smaller environmental impact, in that they are biodegradable and renewable and give rise to less toxic combustion by-products.

However in contrast to these advantages the said ester-based oils normally have a high viscosity and a high pour point, which limit the possibilities for their use. The viscosity and pour point of an oil should in fact be sufficiently low to ensure effective and uniform heat dispersion and low-temperature fluidity. These properties may be modulated by acting on the length and branching of the molecules; however this generally gives rise to a difficult balance between other properties, causing in particular a reduction in high-temperature properties, such as flash point. A high flash point and low volatility are instead important indicators of stability and safety, in that they reduce the risk of fire and explosion and therefore constitute determining factors when evaluating performance of the oil.

It has now surprisingly been found that trimethylolpropane esters with linear and branched monocarboxylic acids having nine and/or ten carbon atoms with a percentage of branched acids of 5-15% in moles in comparison with total monocarboxylic acids have a combination of viscosity values and flash points associated with particularly low pour points which render them particularly suitable for use as transformer oils without the need for specific additives to change such properties.

The present invention therefore refers to trimethylolpropane esters with monocarboxylic acids having nine and/or ten carbon atoms, the said monocarboxylic acids of nine and/or ten carbon atoms comprising 5-15% in moles of branched acids and 85-95% in moles of linear acids with respect to the total moles of monocarboxylic acids, which have viscosity, pour point and flash point properties rendering them particularly suitable for use as transformer oil.

The said branched acids are saturated and unsaturated monocarboxylic acids having nine carbon atoms (C9) and/or ten carbon atoms (C10) having branches along the chain, the said branched acids being the same or different. Examples are 3,5,5-trimethylhexanoic acid, 7-methyloctanoic acid, 2,2-dimethylheptanoic acid, 3,3-dimethylheptanoic acid, 8-methylnonanoic acid, 2,2-dimethyloctanoic acid and mixtures thereof. 3,5,5-trimethylhexanoic acid is particularly preferred.

The branched C9 and/or C10 monocarboxylic acids constitute the 5-15% of the total moles of monocarboxylic acids, preferably the 8-12%, more preferably the 9-11% of the total moles of monocarboxylic acids.

The said linear acids are monocarboxylic acids having nine carbon atoms (C9) and/or ten carbon atoms (C10) with a linear chain, preferably having nine carbon atoms. Acids originating from renewable sources, for example pelargonic acid obtained from processes of the oxidative cleavage of fatty acids, vegetable oils or their derivatives such as those described in patent applications EP 666 838, EP 2 155 646, EP 1 926 699, WO 2011/080296, WO 2011/080297, WO 2013/079849 are preferred. Also preferred are saturated C9 monocarboxylic acids with a purity of preferably more than 95% and preferably containing less than 3% of octanoic acid and less than 3% of decanoic acid.

The linear carboxylic acids constitute the 85-95%, preferably the 88-92%, more preferably the 89-91% of the total moles of monocarboxylic acids.

It has been observed that trimethylolpropane esters with only linear C9 monocarboxylic acids have pour points of not less than −42° C., and are therefore not very suitable for use as low temperature transformer oils. Surprisingly the presence of a quantity of branched C9 or C10 acids of between 5 and 15% brings about an appreciable fall in the pour point. For example, in the presence of 10% of branched C9 acids the pour point of the ester falls below −50° C., while the flash point nevertheless remains at about or above 220° C., thus remaining comparable with commonly used transformer fluids.

Conversely the presence of branched acids in a quantity over 15% in moles in relation to total monocarboxylic acids tends to cause both the pour point and kinematic viscosity to increase, limiting their window of applicability as insulating oils.

As far as physical properties are concerned, the ester according to this invention has a density at 20° C. which is preferably less than 950 kg/dm$^3$ measured according to standard IS03675. Kinematic viscosity, understood to be the ratio between the dynamic viscosity of a liquid and its density, at 40° C. is preferably less than 35 mm$^2$/s, more preferably less than 30 mm$^2$/s, even more preferably less than 25 mm$^2$/s, when measured according to standard ISO 3104.

The pour point is below −40° C., advantageously below −45° C., preferably below −48° C. and even more preferably below −51° C. according to standard ISO 3016.

The flash point according to standard ISO 2719 (Pensky-Martens, closed cup procedure) is preferably above 200° C.

As far as electrical properties are concerned, the oil/ester has a breakdown voltage of preferably more than 70 kV and more preferably over 80 kV in accordance with standard IEC 60156, a dissipation factor (tan δ at 90° C.) preferably below 0.03 and a resistivity preferably higher than 4 GΩ×m at 90° C. and more preferably above 5 GΩ×m at 90° C., the latter being measured in accordance with standard IEC 60247. In order to ensure that the oil/ester achieves the abovementioned electrical properties it is preferable that the water content should be below 100 mg/kg (measured in accordance with standard IEC 60814) and that total acidity should be less than 0.03 mg KOH/g (measured in accordance with standard IEC 62021-1 or IEC 62021-2).

The esters according to the invention advantageously biodegrade quickly, and this can for example be measured using the OECD ("Organization for Economic Cooperation and Development") test 301 B.

The trimethylolpropane esters with monocarboxylic acids having nine and/or ten carbon atoms according to the invention may be prepared by any method known to those skilled in the art, starting for example from linear and branched monocarboxylic acids, their esters or acyl halides.

According to one aspect of the invention these are prepared by esterification or transesterification reactions catalysed by means of acid, basic or enzyme catalysts. Suitable catalysts are for example acids such as hydrochloric, sulfuric, sulfonic (e.g. methanesulfonic, para-toluenesulfonic), or phosphoric acids and Lewis acids.

According to another aspect of the invention the esters are prepared by means of esterification reactions in the absence of catalyst.

According to a preferred aspect of the invention the said esters are prepared from acids without catalyst, using an excess of the acid component in comparison with the moles of polyol hydroxyls (for example 25-30%) at a temperature of up to 240° C. and removing the water formed in the course of the reaction in a manner known in the art. The excess acids are then removed on completion of the reaction.

The object of this invention is therefore also a process for the preparation of esters comprising the esterification of trimethylolpropane with monocarboxylic acids having nine and/or ten carbon atoms, comprising 5-15% in moles of branched chains and 85-95% in moles of linear chains, the said esterification being preferably performed in the absence of catalyst.

Another object of this invention is a process for the preparation of esters comprising the transesterification of trimethylolpropane with alkyl esters of monocarboxylic acids having nine and/or ten carbon atoms comprising 5-15% in moles of branched chains and 85-95% in moles of linear chains, the said alkyl esters being for example methyl esters, ethyl esters, propyl esters, butyl esters or their mixtures. Advantageously trimethylolpropane is transesterified with methyl esters of monocarboxylic acids.

Advantageously the esterification of the trimethylolpropane hydroxyl groups is total, the hydroxyl number of the resulting ester being preferably equal to or less than 2 mg KOH/g.

The presence of moisture or impurities has a notable influence on the oxidation stability of an insulating oil and its electrical properties. For the purposes of use as insulating oils trimethylolpropane esters according to this invention therefore advantageously undergo purification treatments with a view for example to reducing the water content and free acidity or unreacted hydroxyl groups and to obtain a clear liquid free from suspended solids and sediments. Suitable treatments comprise for example dehydration, decolouring, deacidification and filtration operations. The latter may be performed using silica gel, activated carbons, basic alumina and their combinations. For example moisture and/or polar substances are typically adsorbed onto phyllosilicates known as Fuller's earths, such as for example attapulgite, bentonite and sepiolite.

Depending upon its application and the performance required, the ester to which this invention relates may be used as an insulating oil as such and/or with additives and/or mixed with other insulating oils.

This invention therefore also relates to insulating oils comprising, or advantageously consisting of, trimethylolpropane esters with monocarboxylic acids having nine and/or ten carbon atoms comprising 5-15% in moles of branched acids and 85-95% in moles of linear acids in comparison with total monocarboxylic acids.

In accordance with one particularly advantageous aspect this invention relates to an insulating oil comprising the said esters and one or more additives. The said insulating oil has a kinematic viscosity at 40° C. of less than 35 mm$^2$/s, a pour point of below −40° C. and a flash point of over 200° C., even without the addition of additives to alter low-temperature fluidity or flash point. A preferred example is an insulating oil comprising the said esters and one or more additives having an antioxidant action.

In accordance with another aspect this invention relates to mixtures of insulating oils comprising the said esters.

The term "insulating oil" in this description comprises oils or fluids for transformers, dielectric coolants, oils capable of providing electrical insulation, dissipating heat, lubricating and protecting materials from the action of oxygen, which are therefore suitable for use in electrical equipment.

When the esters according to this invention are used in a mixture with other insulating oils, they advantageously constitute more than 20%, preferably more than 40%, and more preferably more than 70% by weight of the total mixture.

Examples of other insulating oils which may be used in a mixture with the trimethylolpropane esters described above are mineral oils, monoaromatic hydrocarbons, silicone oils, aromatic ethers, natural ester-based compounds and/or synthetic ester-based compounds which are different from those which are the subject matter of this invention.

Examples of natural ester-based compounds are vegetable or animal oils, which may or may not be modified. The said oils typically contain mixtures of linear or branched fatty acid glycerides which may contain one or more unsaturations, preferably containing at least one unsaturation. Vegetable oils such as for example soya oil, sunflower, palm oil, cocoa oil, brassicacea oil, maize oil, peanut oil, cottonseed oil, olive oil, safflower oil, milk thistle oil, jojoba oil, lesquerella oil, limnanthes oil and their mixtures are advantageously used as mixtures with the oil according to the invention. Particularly preferred are versions of such vegetable oils which have an oleic acid content of more than 75% and preferably more than 80%.

Examples of synthetic ester-based compounds are polyol esters and diesters.

The said polyols may for example be neopentylglycol, trimethylolpropane, trimethylolethane, glycerol, pentaerythritol, their oligomers (such as for example diglycerol, ditrimethylolpropane, dipentaerythritol) or their mixtures, esterified with monocarboxylic or dicarboxylic acids having a C5-C18 chain; preferably linear or branched saturated and unsaturated monocarboxylic acids such as for example pentanoic, hexanoic, heptanoic, octanoic, 2-ethylhexanoic, nonanoic, decanoic, undecanoic, dodecanoic or lauric, tridecanoic, tetradecanoic or myristic, pentadecanoic, palmitic, palmitoleic, heptadecanoic, stearic or oleic acids and their mixtures are preferably used. Examples of mixtures of preferred monocarboxylic acids are mixtures of C5-C9 acids which can advantageously be obtained by the oxidative cleavage processes of fatty acids, vegetable oils or their derivatives, such as those described in patent applications EP 666 838, EP 2 155 646, EP 1 926 699, WO 2011/080296, WO 2011/080297, WO 2013/079849. Examples of dicarboxylic acids are adipic, azelaic, sebacic, dodecandioic, or phthalic acids or dimer acids.

The said diesters include for example esters of dicarboxylic acids such as adipic, azelaic, sebacic, dodecandioic, or phthalic acids or dimer acids with monoalcohols such as octyl, isooctyl, 2-ethylhexyl, isononyl, isodecyl and tridecyl alcohols.

Other ester-based compounds which may be present in the mixture with the insulating oils according to the invention are monoesters and monocarboxylic acids such as for example fatty acid methyl esters.

This invention also relates to an electrical apparatus comprising the said insulating oils and a method for preparing an insulating oil from trimethylolpropane esters with monocarboxylic acids having nine and/or ten carbon atoms comprising 5-15% in moles of branched acids and 85-95% in moles of linear acids with respect to total monocarboxylic acids, the said method preferably comprising at least one purification operation selected from those described above and optionally the addition of one or more additives.

When the esters according to this invention are used as insulating oils, one or more additive may be added to them as known in the art to further increase their properties. Examples of commonly used additives are antioxidants, antistatic agents, hydrolysis inhibitors, antimicrobial agents, antifoaming agents, metal passivators such as for example triazoles, extreme pressure additives, pour point depressants, anti-wear additives (e.g. zinc dithiophosphate).

Antioxidants or oxidation inhibitors are typically amine and/or phenol based, and may be selected for example from bis-hydroxytoluene, hydroxytoluene butylate, hydroxyanisole butylate, t-butyl catechol, propyl gallate, hydroquinone, t-butyl hydroquinone, naphthol, and phenylnaphthylamine.

By hydrolysis inhibitors are meant for example carbodiimides, which act as acid scavengers.

The said additives may be added, individually or in a mixture, each in a quantity preferably equal to or less than 5%, more preferably equal to or less than 0.5% by weight with respect to the weight of the insulating fluid.

The esters according to this invention comprise insulating oils with high performance at low and high temperatures which also make them suitable for severe climates. Possible specific applications as insulating oils include use in distribution transformers and power transformers.

Some examples and embodiments of this invention, which are to be considered to be illustrative and not limiting upon it, will now be provided.

EXAMPLES

Example 1

A trimethylolpropane ester with carboxylic acids having nine carbon atoms according to the invention was prepared by placing:

26.3 g of trimethylolpropane, 108 g of nonanoic acid (purity >99%)

12 g of 3,5,5-trimethylhexanoic acid (linear:branched acid molar ratio=90:10) in a glass reactor equipped with an electric heating jacket, a condenser and a mechanical stirrer.

During the synthesis the temperature of the reaction medium was increased to 240° C.

During the final reaction stage the pressure was reduced to 200 mbar to encourage the removal of water. On completion of the reaction the product was purified, the excess acids being evaporated by means of a further reduction in pressure to 10 mbar and the residual acidity neutralised by treatment with calcium hydroxide.

The product underwent a further purification treatment using a Fuller's earth (sepiolite) and A4 molecular sieves in order to reduce the acidity and water content.

Table 1 shows the properties of the product obtained, measured according to the methods indicated, before and after the addition of a quantity of 0.3% by weight of a primary phenol antioxidant (Irganox® 1010, marketed by BASF SE):

TABLE 1

| ANALYSIS | METHOD | TMP-C9<br>C9-isoC9 = 90:10<br>without additive | TMP-C9<br>C9-isoC9 = 90:10<br>with additive |
|---|---|---|---|
| Appearance | VISUAL | Clear liquid free of suspended solids | Clear liquid free of suspended solids |
| Viscosity at 40° C. (mm²/s) | ISO 3104 | 21.39 | 21.39 |
| Density at 15° C. (g/ml) | ISO3675 | 0.944 | 0.944 |
| Pour point (° C.) | ISO 3016 | <−54 | <−54 |
| Water content (ppm) | IEC 60814 | 46.7 | 36.7 |
| Discharge voltage (2.5 mm gap) (kV) | IEC 60156 | 86 | 77 |
| Dissipation factor (tan δ 90° C.) | IEC 60247 | 0.03084 | 0.02854 |
| Resistivity (GΩ × m at 90° C.) | IEC 60247 | 6.3 | 6.2 |
| Total acidity (mgKOH/g) | IEC 62021-1 | 0.0101 | 0.0039 |
| Flash point (closed cup) (° C.) | ISO 2719 | 220 | — |

On the basis of the properties measured the product obtained is therefore suitable for use as transformer oil. In particular, in comparison with a trimethylolpropane ester with a nonanoic acid (which has a viscosity of 20.5 mm²/s and a pour point of −42° C. measured under the same conditions) the ester according to the invention has similar viscosity values and a significantly lower pour point. Together with these viscosity and pour point values the ester according to the invention has a flash point which is in any event over 200° C., in line with that of ester-based insulating oils in common use.

Examples 2-3

Two trimethylolpropane esters with carboxylic acids having nine carbon atoms according to the invention were prepared in the same manner as in Example 1 but varying the linear: branched acid molar ratio from 95:5 (Example 2) to 85:15 (Example 3).

Thus respectively 114 g of nonanoic acid and 6 g of 3,5,5-trimethylhexanoic acid in Example 2 and 102 g of nonanoic acid and 18 g of 3,5,5-trimethylhexanoic acid in Example 3 were esterified with 26.3 g of trimethylolpropane.

The kinematic viscosity at 40° C., pour point and flash point properties of the obtained products (without additives), measured according to the same methods indicated in Table 1, are comparable to those of Example 1, as shown in Table 2.

Example 4

A trimethylolpropane ester with carboxylic acids having nine and ten carbon atoms according to the invention was prepared in the same operating manner as in Example 1 by esterifying:
26.3 g of trimethylolpropane,
108,8 g of nonanoic acid (purity >99%)
13,7 g of iso-decanoic acid (linear:branched acid molar ratio=90:10).

After purification treatment using a Fuller's earth (sepiolite) and A4 molecular sieves, the viscosity at 40° C. (according to ISO 3104), pour point (according to ISO 3016) and Flash point (closed cup; according to ISO 2719) of the resulting ester were measured. Results are reported in Table 2.

Example 5—Comparative

A trimethylolpropane ester with carboxylic acids having nine carbon atoms and a linear: branched acid molar ratio of 10:90 was prepared in the same operating manner of Example 1, by esterifying
26.3 g of trimethylolpropane,
12 g of nonanoic acid (purity >99%)
108 g of 3,5,5-trimethylhexanoic acid.

As can be seen from Table 2, the resulting trimethylolpropane esters of Example 5-comparative showed a viscosity at 40° C. considerably higher than 35 mm$^2$/s and a pour point temperature above −45° C., which render them unsuitable for use as transformer oil.

The invention claimed is:

1. An ester of trimethylolpropane with monocarboxylic acids of nine and/or ten carbon atoms, said monocarboxylic acids of nine and/or ten carbon atoms comprising 5-15 mol % of a branched acid and correspondingly 85-95 mol % of pelargonic acid with respect to the total moles of the said monocarboxylic acids, said ester having a kinematic viscosity at 40° C. of less than 35 mm$^2$/s and having a pour point according to standard ISO 3016 of below −40° C.

2. The ester according to claim 1 having a kinematic viscosity at 40° C. of less than 30 mm$^2$/s.

3. The ester according to claim 1 having a pour point according to standard ISO 3016 of below −45° C.

4. The ester according to claim 1 having a flash point according to standard ISO 2719 (Pensky-Martens, closed cup procedure) of above 200° C.

5. The ester according to claim 1 wherein said branched acid is selected from 3,5,5-trimethylhexanoic acid, 7-methyloctanoic acid, 2,2-dimethylheptanoic acid, 3,3-dimethylheptanoic acid, 8-methylnonanoic acid, 2,2-dimethyloctanoic acid and mixtures thereof.

6. The ester according to claim 1 having an hydroxyl number equal to or less than 2 mg KOH/g.

7. A process for the preparation of an ester according to claim 1 comprising the esterification of trimethylolpropane with monocarboxylic acids of nine and/or ten carbon atoms comprising 5-15 mol % of a branched chain and 85-95 mol % of pelargonic acid.

8. The process according to claim 7 wherein said esterification is carried out in the absence of catalyst.

9. A process for the preparation of an ester according to claim 1 comprising the transesterification of trimethylolpropane with alkyl esters of monocarboxylic acids having nine and/or ten carbon atoms comprising 5-15 mol % of a branched chain and 85-95 mol % of pelargonic acid.

10. An insulating oil comprising an ester according to claim 1 and an additive and/or another insulating oil.

11. An insulating oil comprising an ester of trimethylolpropane according to claim 1.

12. The insulating oil according to claim 11 further comprising one or more additives selected from the group consisting of antioxidants, antistatic agents, hydrolysis inhibitors, antimicrobial agents, antifoaming agents, metal passivators, extreme pressure additives, pour point depressants, and anti-wear additives.

13. The ester according to claim 2 having a pour point according to standard ISO 3016 of below −45° C.

14. The ester according to claim 2 having a flash point according to standard ISO 2719 (Pensky-Martens, closed cup procedure) of above 200° C.

TABLE 2

| ANALYSIS | Example 2 (C9:iso-C9 = 95:5) | Example 3 (C9:isoC9 = 85:15) | Example 4 (C9-isoC10 = 90:10) | Example 5- comparative (C9:isoC9 = 10:90) |
|---|---|---|---|---|
| Appearance | Clear liquid free of suspended solids | Clear liquid free of suspended solids | Clear liquid free of suspended solids | Clear liquid free of suspended solids |
| Viscosity at 40° C. (mm$^2$/s) | 21.49 | 22.29 | 21.07 | 44.31 |
| Pour point (° C.) | −48 | <−55 | −47 | −42 |
| Flash point (closed cup) (° C.) | 222 | 225 | 227 | 229 |

15. The ester according to claim 3 having a flash point according to standard ISO 2719 (Pensky-Martens, closed cup procedure) of above 200° C.

16. The ester according to claim 2 wherein said branched acid is selected from 3,5,5-trimethylhexanoic acid, 7-methyloctanoic acid, 2,2-dimethylheptanoic acid, 3,3-dimethylheptanoic acid, 8-methylnonanoic acid, 2,2-dimethyloctanoic acid and mixtures thereof.

17. The ester according to claim 3 wherein said branched acid is selected from 3,5,5-trimethylhexanoic acid, 7-methyloctanoic acid, 2,2-dimethylheptanoic acid, 3,3-dimethylheptanoic acid, 8-methylnonanoic acid, 2,2-dimethyloctanoic acid and mixtures thereof.

18. The ester according to claim 1, wherein said branched acid is selected from 3,5,5-trimethylhexanoic acid.

19. The ester according to claim 18, which comprises 8-12 mol % of the branched acid and correspondingly 88-92 mol % of pelargonic acid with respect to the total moles of the said monocarboxylic acids.

20. The ester according to claim 18, which comprises 9-11 mol % of the branched acid and correspondingly 89-91 mol % of pelargonic acid with respect to the total moles of the said monocarboxylic acids.

21. The ester according to claim 1, which comprises 8-12 mol % of the branched acid and correspondingly 88-92 mol % of pelargonic acid with respect to the total moles of the said monocarboxylic acids.

22. The ester according to claim 1, which comprises 9-11 mol % of the branched acid and correspondingly 89-91 mol % of pelargonic acid with respect to the total moles of the said monocarboxylic acids.

23. The ester according to claim 1 having a kinematic viscosity at 40° C. of less than 25 mm$^2$/s and having a pour point according to standard ISO 3016 of below −51° C.

24. A method for preparing an insulating oil, from a trimethylolpropane ester with monocarboxylic acids having nine and/or ten carbon atoms, said monocarboxylic acids of nine and/or ten carbon atoms comprising 5-15 mol % of a branched acid and 85-95 mol % of correspondingly pelargonic acid with respect to the total moles of the said monocarboxylic acids, said ester having a kinematic viscosity at 40° C. of less than 35 mm$^2$/s and having a pour point according to standard ISO 3016 of below −40° C.; comprising at least one purification operation selected from the group consisting of dehydration, decolouring, deacidification and filtration.

25. An electrical apparatus comprising at least one insulating oil according to claim 11.

* * * * *